United States Patent [19]
Kaluza et al.

[11] Patent Number: 5,973,123
[45] Date of Patent: Oct. 26, 1999

[54] IMMUNOASSAY FOR THE DETECTION OF MIA

[75] Inventors: Brigitte Kaluza, Bad Heilbrunn; Iise Bartke, Bernried; Helmut Lenz, Tutzing; Martin Kaufmann, Weilheim; Reinhard Büttner, Bach/Donau; Anja-Katrin Bosserhoff, Regensburg, all of Germany

[73] Assignee: Roche Diagnostics GmbH, Mannheim, Germany

[21] Appl. No.: 08/993,092

[22] Filed: Dec. 18, 1997

[30] Foreign Application Priority Data

Dec. 20, 1996 [DE] Germany ............ 196 53 358

[51] Int. Cl.[6] .......... C07K 16/18; C07K 16/24; G01N 33/53; G01N 33/536
[52] U.S. Cl. .............. 530/388.24; 530/387.3; 530/387.1; 530/387.7; 530/388.1; 530/388.8; 530/388.85; 436/547; 435/7.1; 435/7.21; 435/7.23; 435/7.9; 435/7.93; 435/7.94; 435/70.1; 435/172.2
[58] Field of Search ............... 435/7.1, 7.23, 435/7.9–7.95, 7.21, 7.93, 7.94, 70.1, 172.2; 530/387.1, 387.3, 387.7, 388.1, 388.8, 388.24, 388.25; 436/547

[56] References Cited

U.S. PATENT DOCUMENTS 5,770,366  6/1998  Bogdahn et al. ............ 435/6

FOREIGN PATENT DOCUMENTS

95/03328  2/1995  WIPO.

OTHER PUBLICATIONS

CA 125:237905, 1995.
Harlow and Lane, Antibodies, A Lab manual, pp. 27–28, 1988.
Blesch et al., Proceedings of the American Association for Cancer Research, vol. 35, Mar. 1994, p. 567, "Expression and function of a novel, potent malignant melanoma cell . . . ".
Bosserhoff et al., Cancer Research, vol. 57, No. 15, Aug. 1, 1997, pp. 3149–3153, "Melanoma–inhibiting activity, a novel serum marker for progression of malignant melanoma."
Hau et al., Proceedings of the American Association for Cancer Research, vol. 38, Mar. 1997, "Evidence for an alternative splice product of MIA/CD–RAP."

*Primary Examiner*—Paula K. Hutzell
*Assistant Examiner*—Nancy Johnson
*Attorney, Agent, or Firm*—Nikaido Marmelstein Murray & Oram, LLP.

[57] ABSTRACT

The subject matter of the present invention are high-affinity monoclonal antibodies against MIA (Melanoma inhibitory activity) in native conformation, which can be used for the detection of malignant melanomas, their use for the detection of MIA as well as immunoassays for the detection of MIA.

15 Claims, No Drawings

IMMUNOASSAY FOR THE DETECTION OF MIA

The present invention concerns high-affinity, monoclonal antibodies against MIA (Melanoma Inhibitory Activity), their use for the detection of MIA and immunoassays for the detection of MIA.

MIA (Melanoma Inhibitory Activity) is a soluble protein which has a size of 11 kDa and is secreted by malignant melanoma cells. A malignant melanoma is a malignant tumor resulting from the pigment-producing skin cells called melanocytes and susceptible to the formation of metastases. The healing chances depend on the extent of metastasis and tumor assessment according to the recommendations of the German society of dermatology is done by classification into the clinical states I to IV. State I is a primary tumor without recognizable metastases. The tumor thickness is 1.5 mm. This primary tumor can be eliminated by surgery. In state II metastases have already been formed in the immediate surroundings of the tumor (regional lymphatic glands metastasis). The tumor thickness in state II is 1.5 to 4 mm. Healing chances in state III exist only to a small extent due to metastasis and metastatic invasion of the lymphatic glands in more remote tissues. In state IV practically no healing chances exist because of remote metastasis and the complete invasion of the lymphatic glands by metastases.

The malignant melanoma is a type of cancer attacking more and more people. After elimination of the primary melanoma (state I) the guarantee that the melanoma has been eliminated completely and that no metastases have formed is very important for the patient. The conventional follow-up consists—apart from the regular visual examination of the skin with regard to externally perceptible changes—of the search for metastases inside the body by means of physical measuring procedures such as X-ray, sonotopography, computerized axial tomography and occasionally, also positron emission tomography; these procedures do, however, not recognize tumors with a diameter below 0.5 cm, even in multiple metastasis. In the past the parameters S100 (Guo et al., European J. Cancer 1995, Vol 31 A, No. 6, S. 924–928; v. Schoultz et al., Melanoma Research 1996, Vol 6, S. 133–137; Schultz et al., Zeitschrift f. Hautkrankheiten, H+G1996, Vol 11 (71), S. 870–884) or sICAM-1 (Soluble intercellular adhesion molecule 1) were used as tumor markers. The detection of S100 or sICAM-1 does, however, not correlate reliably with the presence of a melanoma. According to Viac et al. (Cancer Lett. 1993, 72, S. 191–194) the detection of the sICAM-1 marker in particular seems to have almost no clinical significance for the detection of melanomas.

A diagnostically clear parameter that reliably excludes or confirms the metastasis formation of the malignant melanoma especially after the removal of the primary melanoma has not been found until now. A reliable diagnostic assay for the detection of the malignant melanoma is not known according to the state of the art, either.

WO 95/03328 refers to the growth inhibiting properties of MIA especially on tumor tissues, which shows that MIA can be interesting for the therapeutical use. This publication principally refers to the feasibility of antibodies against this protein.

From this resulted the task to provide a reliable parameter for the diagnostic detection of the malignant melanoma and to develop an improved diagnostic assay enabling the control of the clinical course of the disease and the healing process and allowing the performance of a screening with the greatest possible sensitivity for the detection of a malignant melanoma and its metastases.

This task is solved by means of monoclonal antibodies directed against native MIA and binding to this protein with a high affinity.

The monoclonal antibodies can be used in all tests for the detection of a protein known to the expert. When using the test procedure preferred with two antibodies (sandwich-test) the test can be performed as a one-step test, i.e. without any additional washing step for the removal of unbound sample components. This simplified test procedure is especially advantageous in screenings where a large number of samples are to be tested in quick succession.

The affinity constants of the monoclonal antibodies for MIA can for example be determined with the BIACORE® system of Pharmacia. To determine the affinity human native MIA manufactured with recombinant methods can be used. According to the invention monoclonal antibodies have an affinity to human native MIA of at least $10^8$ l/mol, especially preferred of at least $10^9$ l/mol. These high-affinity monoclonal antibodies are extremely suitable for one-step tests where in general the incubation of the sample with the monoclonal antibody is relatively short.

The monoclonal antibodies according to the invention can belong to all immunoglobulin classes (Ig). They preferably belong to the IgG1 class. The coupling of further components such as labels like enzymes or haptens or binding partners, which are necessary for the binding of the antibody to a solid phase in heterogeneous immunoassays, can preferably be carried out with IgG1 antibodies. The production of antibody fragments like e.g. F(ab')$_2$, Fab' or Fab fragments is unproblematic with the IgG1 class too.

According to the invention the term "monoclonal antibody" means the complete antibody as well as all fragments like F(ab')$_2$, Fab' or Fab fragments usually occurring in immunoassays and other uses. The term also includes those antibodies produced by the modification of monoclonal antibodies as far as the antigen-binding property was not decisively affected. Parts of the monoclonal antibodies normally produced from mice can for example be substituted by corresponding human antibody sequences using genetic measures to minimize non-specific bindings in immunoassays.

Procedures for production of such chimeric monoclonal antibodies are familiar to the expert, e.g. from Antibody Engineering, J. Mc Cafferty, H. R. Hoogenboom and D. J. Chiswell, The Practical Approach Series, Series Editor: B. D. Hames, Oxford University Press, 1996.

The antibodies according to the invention can for example be produced from the cell lines mAb<hMIA>M-2.F7.3B1 and mAb<hMIA>M-1.A12.9A1, deposited as DSM ACC 2292 and DSM ACC 2291 (deposit numbers) at the German collection of microorganisms and cell cultures ("Deutsche Sammlung von Mikroorganismen und Zellkulturen (DSMZ) GmbH, Mascheroder Weg 1b, D-38124 Braunschweig) on Dec. 10, 1996.

A further subject matter of the invention are antibodies, preferably monoclonal antibodies which bind in an equivalent way to MIA like the monoclonal antibodies <hMIA>M-2.F7.3B1 and <hMIA>M-1.A12.9A1. To "bind in an equivalent way" means here that these antibodies bind to MIA with the same affinity or with a comparably high affinity as the monoclonal antibodies deposited. This can for example be detected when performing appropriate tests with BIACORE®.

A further subject matter of the invention are antibodies, preferably monoclonal antibodies binding to the same MIA epitopes like the antibodies deposited<hMIA>M-2.F7.3B1 and <hMIA>M-1.A12.9A1. This can be established by determining the cross reactivity of the antibodies using for example the BIACORE® system. Preferably these antibodies also have a high affinity to MIA.

The monoclonal antibodies according to the invention can be produced—as already known—by immunization with isolated MIA (isolated from human tissue or recombinant) in suitable test animals like e.g. mice, rats, rabbits and subsequent fusion of the spleen cells of the immunized animals with myeloma cells. Besides spleen cells as lymphocyte source peripheral blood lymphocytes (PBL) or cells of the lymphatic glands from immunized animals (preferably mouse or rat) can be used.

Alternatively, lymphocytes from human donors (tissue samples of melanoma patients) with antibodies developed against MIA can be immortalized. Such lymphocytes producing anti-MIA antibodies can be immortalized either by fusion with a human myeloma cell line or by Epstein-Barr-virus (EBV) transformation to antibody-producing hybridoma cells (Monoclonal Antibody and Immunosensor Technology, A. M. Campbell, Elsevier Verlag 1991; Monoklonale Antikörper, J. H. Peters, H. Baumgarten, Springer Verlag 1990, Monoclonal Antibody Production Techniques and Applications, ed. Lawrence B. Schook, Marcel Dekker Verlag 1987).

If lymphocytes of human donors with antibodies against MIA developed as a result of a melanoma are applied the use of appropriate MIA in the screening procedure for antibody-secreting fusion cells must be considered. Renatured, i.e. native, non-denatured MIA is used preferably.

If the production of the antibodies according to the invention is performed according to the procedure mentioned first, i.e. by immunization of animals and subsequent fusion of the lymphocytes with myeloma cells the origin or the purification of the immunogene and the subsequent screening procedure become particularly important.

Thus, by immunization of mice with peptides derived from the N- and C-terminal amino acid sequence of MIA (AS-position 1-12 and 94-107 respectively) monoclonal antibodies could be prepared. The resulting antibodies did, however, recognize native MIA only with an affinity in the range of $10^6$ l/mol (BIACORE® system). Presumably, these antibodies recognized linear epitopes and no conformation epitopes. If immunization was performed with recombinant MIA renatured to native conformation (according to the invention described in WO 95/03328) monoclonal antibodies could be produced showing an affinity constant of only $10^6$ to $10^7$ l/mol when binding to MIA in the BIACORE® system.

The purification or the screening for hybridoma lines which secreted the desired antibodies against MIA was—in this case—performed with the aid of MIA immobilized by spontaneous adsorption to micro-titer plates.

The high-affinity monoclonal antibodies against native MIA according to the invention could be obtained due to the use of recombinant human native MIA as an immunogene. The MIA was prepared from the expression plasmid p11379 deposited as DSM 9267 (deposit number) at the DSMZ on Jun. 29, 1994 (s. also WO 95/03328). MIA was processed under renaturing conditions so that native, non-denatured MIA was received. The purification, i.e. screening for hybridoma cells which secreted the antibodies against MIA wanted was performed with biotinylated MIA which had been coupled with micro-titer plates via streptavidin. The native conformation of MIA seems to remain when biotinylating so that high-affinity antibodies against human native MIA could be obtained in this screening method. In contrast to that, MIA seems to denature when the screening method mentioned above by means of MIA which is bound to plastic surfaces via spontaneous adsorption is used so that antibodies recognizing (native) conformation epitopes on the MIA protein are not detected.

The invention therefore in addition concerns a method to produce high-affinity monoclonal antibodies against MIA wherein immunization is performed with human, native MIA produced by recombinant means and screening of the hybridoma cell line obtained is carried out using MIA in native conformation.

With this method monoclonal antibodies having an affinity constant regarding the binding of MIA of at least $10^8$ l/mol are used preferably and those of at least $10^9$ l/mol especially preferably.

The invention additionally concerns the use of monoclonal antibodies according to the invention for the diagnostic detection of MIA in samples, preferably human samples such as e.g. plasma, serum, blood, saliva, urine, liquor, lymph, mother milk, cysts, seminal fluid, tissue homogenates, tissue slices and biopsy material.

Another subject matter of the invention is a method to determine MIA by incubation of the sample with at least one monoclonal antibody according to the invention. All usual protein detection methods known to the expert, like e.g. competitive tests or direct tests like sandwich tests are suitable. Besides heterogeneous tests with assay components bound to a solid phase and isolation of the solid and the liquid phase homogeneous tests can also be used as far as they are suitable for the detection of a protein. Examples of these assays are nephelometric or turbidimetric tests like latex agglutination tests or TINIA (turbidimetric inhibition immunoassay). Apart from the so-called wet tests with test reagents in a liquid phase all remaining usual dry test formats suitable for the detection of a protein can be used. These dry tests or test strips use test components fixed on a carrier. Such dry tests are for example described in EP-A-0 186 799.

The procedures preferred include the sandwich test where the sample is simultaneously incubated with two monoclonal antibodies according to the invention where one is capable of binding to a solid phase and the other carries a label. For this procedure it is important that both monoclonal antibodies applied recognize MIA epitopes which have a position on the MIA protein that allows simultaneous binding of both antibodies to MIA. For that reason different epitopes, i.e. epitopes of different structures are preferably suitable for this procedure. Antibodies recognizing identical epitopes can, however, be used too if the epitopes have a position that allows simultaneous binding of both antibodies to MIA. After isolation of the solid phase from the liquid phase the label is determined according to a method known to the expert. To receive quantifiable test results the expert will, in general, determine several standards of known MIA concentrations together with sample measuring and quantify the MIA concentration of the sample by means of the resulting calibration curve or line.

The MIA detection tests according to the invention allow a reliable proof of the presence of a malignant melanoma. In a clinical study a clear correlation between an increased MIA concentration in the serum and the progression of the state of disease could be observed (see example 6). Starting from a cut-off value of 6.5 ng MIA per ml (95% of a healthy normal group are below this value) 14% of the patients showed already in state I increased MIA serum concentrations. In state II 40% of the sera showed increased MIA concentrations, in state III and IV even 100% of the patient sera.

The invention is further described in the following examples:

EXAMPLE 1
Production of the Immunogene

The immunogene, i.e. recombinant MIA was produced from inclusion bodies containing insoluble MIA. These were obtained by transferring the expression plasmid p11379 into a suitable expression strain of the bacterium *Escherichia coli* and state of the art fermenting; by specific induction the MIA production was induced and the inclusion bodies were obtained by breaking the cells and centrifugation. The expert knows this method well and no further explanations are necessary here. Since MIA was only present as an insoluble aggregate it had to be transformed into a soluble, native form. According to the invention this was not achieved before the introduction of additional stabilizing substances.

For this, 1.5 g of the inclusion bodies in 150 ml of buffer hydrochloride, 100 mmol/l Tris/HCl, pH 8.0, 200 mmol/l dithioerythrol (DTE) and 1 mmol/l ethylenediaminetetraacetic acid (EDTA) were dissolved by ultrasonic treatment and incubation at 25° C. for 1 hour. Then the pH was decreased to 3.0 by adding 25% (v/v) HCl. Afterwards the solution was dialyzed over night against the aforementioned buffer but adjusted to a pH of 3.0 and without addition of DTE. The dialyzate obtained was diluted 1:200 in a buffer containing 1 mol/l arginine, 1 mmol/l EDTA, 5 mmol/l reduced glutathione (GSH) and 500 $\mu$mol/l oxidized glutathione (GSSG) and then incubated at 25° C. for 24 hours.

For further purification this solution was brought to an ammonium sulfate concentration of 1.4 mol/l by adding solid ammonium sulfate and then mixed with an exchange matrix (Fractogel TSK-butyl-650 [M] [Merck KGaA, 16873]) equilibrated in 1.4 molar ammonium sulfate and then incubated for 1 hour. The exchanger was filtrated and washed with 1.4 molar ammonium sulfate in 20 mmol/l Tris, pH 7.0 and filled into a glass column. Elution of the MIA protein was carried out by means of a declining gradient of ammonium sulfate, from 1.4 mol/l in 20 mmol/l Tris, pH 7.0 to 20 mmol/l Tris, pH 7.0.

The resulting MIA was used as an immunogene.

EXAMPLE 2
Production of the Monoclonal Antibodies

BALB/C mice were immunized intraperitoneally with 100 $\mu$g rec. native MIA. Primary immunization was carried out in complete Freund's Adjuvants (CFA)—the remaining immunizations in incomplete Freund's Adjuvants (IFA). Immunization was performed at 4-week intervals. The last three immunizations were carried out intravenously (i.v.) at 1-day intervals. After the last immunization the spleen cells of the immunized animals were immortalized with the myeloma cell line P3X63.Ag8.653.

The fusion of the spleen cells with the myeloma cell line is performed according to the standard procedure by Goding, J. W., J. of Imm.Meth., 39 (1980) 285–308. The fusion ratio spleen cells:myeloma cells is 1:1. The fusion products are sown on 24-well culture plates (Nunc) with HFCS (Boehringer Mannheim GmbH, cat. No. 1363735). Positive primary cultures are cloned two weeks after fusion using a fluorescence-active cell sorter (Beckton Dickinson). For this, the cells are individually transferred to 96-well micro-titer plates and fed with Nutridoma CS-medium (Boehringer Mannheim GmbH, cat. No. 1363743). Subsequently, commercially available RPMI 1640 with 10% fetal calf serum is used as culture medium.

EXAMPLE 3
Determination of Specificity of the Antibodies Produced

To determine the specificity of the antibodies contained in the culture supernatant of the hybridoma cells an enzyme-linked immuno-sorbent assay (ELISA) is carried out.

For this, 96-well streptavidin-coated micro-titer plates (Boehringer Mannheim GmbH, cat. No. 1734776) are covered with 50 $\mu$l of recombinant native biotinylated MIA (1 $\mu$g/ml) in carbonate buffer (Boehringer Mannheim GmbH, cat. No. 726559) at 37° C. for 1 h, incubated with 50 $\mu$l of culture supernatant at 37° C. for 2 h and washed with 3×250 $\mu$l of PBs/0.05% Tween 20. The following steps are incubation with POD-labelled sheep anti-mouse IgG (Boehringer Mannheim) at 37° C. for 60 minutes, washing with 3×250 $\mu$l PBS/0.05% Tween 20 and initiation of the detection reaction using 50 $\mu$l ABTS (1 mg/ml, Boehringer Mannheim GmbH, cat. No. 1204 530). After incubation at room temperature for 20 minutes extinctions are determined in a photometer at 405 nm.

EXAMPLE 4
Determination of Affinity Constants and Rate Constants of the Association and Dissociation of the Antibodies Produced The determination of affinity constants and rate constants of the association and dissociation of the antibodies produced was carried out with BIACORE® of the company Pharmacia Biosensor (BIA means Biospecific Interaction Analysis). The measuring principle is based on the "Surface Plasmon Resonance". Measuring is carried out on a biosensor, called sensor chip. A polyclonal rabbit antibody against the Fc$\gamma$-part of mouse IgG is coupled by covalent binding of its aminogroups to the surface of a sensor chip coated with carboxymethylated dextrane. A solution of the antibody to be determined is passed over this sensor chip, whereby antibody is bound to the immobilized scavenging antibody by non-covalent interaction forces. The antigen to be determined is then passed over the sensor chip and also bound to the antibody immobilized by the scavenging antibody by non-covalent interaction forces.

The binding of the single components increases the mass density on the surface of the sensor chip which is converted into a proportional measuring signal. The rate constants of the association and dissociation and from this the affinity constant are calculated from the time dependent change of the signal, the sensor graph.

The antibody-antigen complexes can be separated by means of simple methods without affecting the scavenging antibody bound to the surface so that further binding experiments can be carried out with the same sensor chip and under identical conditions.

To couple the scavenging antibody with the sensor chip (CM5, BIACORE® AB) a solution of the antibody (BIA certified Rabbit anti Mouse Fc$\gamma$, BIACORE® AB) with a concentration of 60 $\mu$g/ml in 10 mM sodium acetate buffer, pH 5.0, with a flow rate of 5 $\mu$l/min is passed over the sensor chip previously activated with NHS/EDC.

Afterwards the antibodies are added so that an increase in mass bound to the surface of at least 600 resonance units is obtained. The binding of the antigens to the antibodies is observed with a flow rate of 10 $\mu$l/min and the rate constants of the association and dissociation for the binding to the antibodies from the sensor graphs are calculated with the manufacturer's software (BIAevaluation 2.1, Pharmacia Biosensor). The affinity constant is calculated according to Ka=kon/koff The resulting MIA values of the antibodies according to the invention are listed in the table depicted in the following.

TABLE 1

Affinity constants of the MIA mAb

| | MIA | | |
|---|---|---|---|
| Clone | kon 1/mol*s | koff 1/s | Ka 1/mol |
| 1.A12.9A1 | $9.3*10^{+5}$ | $4.2*10^{-4}$ | $2.2*10^{+9}$ |
| 2.F7.3B1 | $5.7*10^{+5}$ | $1.8*10^{-3}$ | $3.2*10^{+8}$ |

EXAMPLE 5
ELISA Test for the Detection of MIA
5.1 Production of the Substances Needed for ELISA a) mAb<MIA>M-2F7-IgG-Biotin(DDS)1:4

The procedure was performed according to the method described in the laid-open documentation DE 43 02 241 A1. Monoclonal anti-MIA-M-2F7-IgG (Boehringer Mannheim GmbH) is dissolved in 0.1 M potassium phosphate buffer, pH 8.4, to a concentration of 10 mg/ml. Four times the molar quantity of biotin-DDS (dissolved in dimethyl sulfoxide ad c=9.5 mg/ml) is added. After agitating at 25° C. for 90 min the preparation is stopped by adding 10 µl 1 M lysine/ml preparation. Subsequently, dialysis against 25 mM potassium phosphate/50 mM NaCl, pH 7.0 is performed and the product is lyophilized.

b) mAb<MIA>M-1A12-IgG-POD(p)

The procedure was performed according to EP 0 378 175 B1. The IgG fraction of the monoclonal anti-MIA antibody was purified from ascites liquid by ammonium sulfate precipitation and chromatography on DEAE ion exchanger according to Johnstone and R. Thorpe, Immunochemistry in Practice, Blackwell Scientific, 1987, pages 50–54. 50 mg purified IgG were transformed with S-acetyl-thio-succinic anhydride and coupled to 50 mg pre-polymerized maleic hexanoyl peroxidase according to the method described in DE-A-38 25 735. By AcA 22 chromatography a conjugate pool with a molecular weight of 2–3 millions was obtained. The yield was approx. 30 mg of protein with 13 KU peroxidase (POD) activity.

c) MIA protein, native

The production of the pure, native MIA protein used as the standard material is described in detail in example 1.

d) Incubation buffer of the MIA ELISA (weight given for one liter)

| | |
|---|---|
| $NaH_2PO_4$ | 0.97 g |
| $Na_2HPO_4$ | 5.88 g |
| Di-Na tartrate | 46 g |
| Synperonic F 68 | 5 g |
| Bovine IgG | 1 g |
| Bovine albumin | 2 g |

The pH value is adjusted to 7.4 using NaOH.

5.2 Description of ELISA

Step I

10 µl standard solution (rec. h-MIA in 50 mmol/l Hepes, 150 mmol/l NaCl, pH 7.0, dilution series with 0, 3.13, 6.25, 12.5, 25, 50 ng/ml) or 10 µl of the sample to be tested (serum, plasma etc.) are transferred to the wells of a micro-titer plate coated with streptavidin (Boehringer Mannheim GmbH, Id. No. 1 664 778). Subsequently, 200 µl of a solution of 1 µg/ml mAb<MIA>M-2F7-Bi and 25 mU/ml mAb<MIA>M-1A10-POD in incubation buffer are pipetted into each well filled with standard or sample. Afterwards, the micro-titer plate is agitated at room temperature (20–25° C.) for 45 minutes on a commercially available agitator for micro-titer plates (e.g. IKA MTS 4) at 500 rpm.

Washing step

The wells of the micro-titer plates are carefully emptied and each washed three times with 300 µl washing solution (250 mg NaCl/l, 1 mg $CuSO_4$/l, Boehringer Mannheim GmbH, Ig. No. 1 059 475).

Step II

200 µl ABTS® substrate solution (2,2'azino-di[3-ethylbenzothiazoline sulfonate] 1.9 mmol/l ABTS®, 100 mmol/l phosphate-citrate buffer, pH 4.4, sodium perborate 3.2 mmol/l) are pipetted into each micro-titer plate well prepared in step 1 and incubated at room temperature (20–25° C.) for 30 minutes on the plate agitator at 500 rpm.

The extinction values of the resulting color solutions in the wells are measured at 405 nm with a photometer suitable for micro-titer plates. A standard curve allowing the reading of the sample concentrations is established from the signals and the concentration values of the standard series.

EXAMPLE 6

Comparison of MIA, S100 and sICAM-1 Tests Regarding Sensitivity

The MIA concentration was determined according to the procedure described in example 4. The S100 concentrations were determined with a commercially available immunoradiometric test of the company Byk-Sangtec Diagnostics, Dietzenbach, Germany (see also Kato et al, Biomed Res. 1987, Vol 8, p. 119–125) according to the manufacturer's specifications. The sICAM-1 values were determined with the one-step ELISA kit of the company Amersham, Braunschweig, Germany, according to the instructions for use.

TABLE 2a

Value ranges determined

| Sera tested Subject group | MIA ng/ml | S100 ng/ml | sICAM-1 ng/ml |
|---|---|---|---|
| Normal | 1.8–7.6 (n = 72) | <0.15 (n = 13) | 220–466 (n = 9) |
| Sepsis | 1.4–6.8 (n = 50) | 0–0.3 (n = 10) | 161–927 (n = 7) |
| Melanoma state I | 2.9–7.7 (n = 14) | <0.15 (n = 14) | — |
| Melanoma state II | 3.6–8.1 (n = 5) | <0.15 (n = 5) | — |
| Melanoma state III | 7.5–24.7 (n = 5) | 0–13.3 (n = 5) | 194–1430 (n = 14) |
| Melanoma state IV | 7.5–64.8 (n = 21) | 0–11.7 (n = 21) | "–" |

"n" is the number of sera tested

These results show that MIA is an excellent marker for evaluation of progressive malignant melanoma. MIA is a marker with sufficient sensitivity for classification of a tumor disease into the states I to IV. This classification is not possible with the markers S100 and sICAM-1. MIA is a much more reliable tumor marker than S100 and sICAM-1. The determination of MIA is not disturbed by sepsis sera (in contrast to sICAM-1).

TABLE 2b

Percentage of sera tested which can be classified into the states I to IV on the basis of the test results of table 2a

| Patient group | MIA % > cut-off (6.5 ng) | S100 % > cut-off (0.15 ng) | sICAM-1 % > cut-off (280 ng) |
|---|---|---|---|
| Normal | 2.7 | 0 | 33 |
| Sepsis | 0 | 20 | 71 |
| Melanoma state I | 14 | 0 | — |
| Melanoma state II | 40 | 0 | — |
| Melanoma state III | 100 | 60 | 43 |
| Melanoma state IV | 100 | 57 | " |

The data shows that the MIA determination indicates more reliably the possible presence of metastases in the states II–IV and can therefore be used for validation of further diagnostic steps and prognosis. From the data can also be derived that in the states III and IV MIA as a melanoma-specific protein correlates better with the tumor mass than S100 or sICAM-1.

We claim:

1. A monoclonal antibody, or fragment thereof, which has an affinity for native melanoma inhibitory activity protein of at least $10^8$ l/mol.

2. The monoclonal antibody, or fragment thereof according to claim 1, wherein said antibody belongs to the IgG1 class.

3. The monoclonal antibody, or fragment thereof, according to claim 1, wherein said antibody is a mouse/human chimeric monoclonal antibody.

4. A monoclonal antibody, or fragment thereof, directed against native melanoma inhibitory activity protein, wherein said monoclonal antibody, or fragment thereof is produced by the cell lines mAB<hMIA>M-2.F7.3B1 (DSM ACC 2292) or mAb<hMIA>M-1.A 12.9A1 (DSM ACC 2291).

5. A monoclonal antibody, or fragment thereof, directed against native melanoma inhibitory activity protein, wherein said monoclonal antibody or fragment thereof has the same affinity for native melanoma inhibitory activity protein as a monoclonal antibody, or fragment thereof, produced from the cell line mAb<hMIA>M-2.F7.3B1 (DSM ACC 2292) or mAb<hMIA>M-1.A 12.9A1 (DSM ACC 2291).

6. A monoclonal antibody, or fragment thereof, directed against native melanoma inhibitory activity protein, wherein said antibody or fragment thereof binds to the same epitopes as a monoclonal antibody, or fragment thereof, produced by the cell line mAb<hMIA>M-2.F7.3B1 (DSM ACC 2292) or mAb<hMIA>M-1.A 12.9A1 (DSM ACC 2291).

7. A method for determining melanoma inhibitory activity protein, comprising incubating a sample with at least one monoclonal antibody according to claim 1 or a F(ab')$_2$, Fab' or Fab fragment thereof to form a complex, and detecting said complex as an indication of the presence of melanoma inhibitory activity protein.

8. The method according to claim 7, wherein said method is a sandwich immunoassay and wherein the at least one monoclonal antibody is produced by the cell lines mAb<hMIA>M-2.F7.3B1 (DSM ACC 2292) and/or mAb<hMIA>M-1.A 12.9A1 (DSM ACC 2291).

9. The method according to claim 7, wherein said at least one monoclonal antibody has the same affinity for melanoma inhibitory activity protein or recognizes the same epitopes as a monoclonal antibody produced by the cell line mAb<hMIA>M-2.F7.3B1 (DSM ACC 2292) and/or mAb<hMIA>M-1.A 12.9A1 (DSM ACC 2291).

10. The method according to claim 7, wherein said complex is detected using a test selected from the group consisting of a nephelometric test, a turbidimetric test, and a turbidimetric inhibition immunoassay.

11. A method for screening for a malignant melanoma, comprising incubating a sample from a patient suspected of having a malignant melanoma with at least one monoclonal antibody according to claim 1 or a F(ab')$_2$, Fab' or Fab fragment thereof, to form a complex, and detecting said complex as an indication of the presence of said malignant melanoma.

12. The method according to claim 10, wherein said sample is selected from the group consisting of plasma, serum, blood, saliva, urine, liquor, lymph, milk, cysts, seminal fluid, tissue homogenates, tissue slices and biopsy material.

13. The method according to claim 12, wherein said sample is serum.

14. A method for monitoring a patient for malignant melanomas, comprising a) obtaining a sample from a patient in need of such monitoring, b) incubating said sample with at least one monoclonal antibody according to claim 1 or a F(ab')$_2$, Fab' or Fab fragment thereof to form a complex, c) detecting said complex as an indication of the presence of a malignant melanoma, and d) repeating steps a)–c).

15. A monoclonal antibody, or fragment thereof, according to claim 1, wherein said antibody is obtained by the following process:

(a) immunizing a test animal with a recombinantly produced human native melanoma inhibitory activity protein in reconstituted native conformation to produce lymphocytes, (b) fusing any lymphocytes produced in step (a) with myeloma cells to produce hybridoma cell lines; and (c) thereafter screening any hybridoma cell lines produced in step (b) for production of the monoclonal antibodies or fragments thereof with a binding affinity for native melanoma inhibitory activity protein using melanoma inhibitory activity protein present in reconstituted native conformation.

* * * * *